United States Patent
Piotrowski et al.

(10) Patent No.: US 7,541,415 B2
(45) Date of Patent: Jun. 2, 2009

(54) PROCESS FOR PREPARING DIARYL ALKYLPHOSPHONATES AND OLIGOMERIC/POLYMERIC DERIVATIVES THEREOF

(75) Inventors: Andrew M. Piotrowski, Yorktown Heights, NY (US); Edward D. Weil, Copley, OH (US); Qiang Yao, Yorktown Heights, NY (US); Sergei V. Levchik, Croton-on-Hudson, NY (US)

(73) Assignee: Supresta LLC, Ardsley, NY (US)

( * ) Notice: Subject to any disclaimer, the term of this patent is extended or adjusted under 35 U.S.C. 154(b) by 0 days.

(21) Appl. No.: 11/661,716

(22) PCT Filed: Aug. 29, 2005

(86) PCT No.: PCT/US2005/030835
§ 371 (c)(1),
(2), (4) Date: Aug. 14, 2007

(87) PCT Pub. No.: WO2006/026616
PCT Pub. Date: Mar. 9, 2006

(65) Prior Publication Data
US 2008/0045673 A1    Feb. 21, 2008

(51) Int. Cl.
*C08G 79/04* (2006.01)
*C08L 85/02* (2006.01)

(52) U.S. Cl. .................. 528/167; 525/534
(58) Field of Classification Search .............. None
See application file for complete search history.

(56) References Cited

U.S. PATENT DOCUMENTS

| 3,261,890 A | | 7/1966 | Gordon et al. | |
|---|---|---|---|---|
| 4,374,971 A | * | 2/1983 | Schmidt et al. | 528/167 |
| 4,377,537 A | * | 3/1983 | Block et al. | 558/122 |
| 4,690,964 A | * | 9/1987 | Schmidt et al. | 524/125 |
| 2005/0020800 A1 | * | 1/2005 | Levchik et al. | 528/108 |

FOREIGN PATENT DOCUMENTS

| EP | 0034239 | 3/1984 |
|---|---|---|
| EP | 0742261 | 11/1996 |
| WO | 03/029258 | 4/2003 |

* cited by examiner

*Primary Examiner*—Robert Sellers
(74) *Attorney, Agent, or Firm*—Dilworth & Barrese, LLP

(57) ABSTRACT

A process is provided for the production of diaryl alkyl phosphonate by the reaction of triaryl phosphate with dialkyl alkyl phosphonate in the presence of alkali metal iodide catalyst; and, optionally, the diaryl alkyl phosphonate is reacted in situ with aromatic diol and, optionally, with at least one branching monomer, in the absence of other or further added catalyst to provide oligomeric and/or polymeric phosphonate products.

16 Claims, No Drawings

PROCESS FOR PREPARING DIARYL ALKYLPHOSPHONATES AND OLIGOMERIC/POLYMERIC DERIVATIVES THEREOF

BACKGROUND OF THE INVENTION

This invention relates to an improved process for making diaryl alkylphosphonates and oligomeric and/or polymeric arylene alkylphosphonate derivatives thereof. The diaryl alkylphosphonates and their oligomeric and polymeric derivatives are useful as flame retardants, e.g., in epoxy resins intended for electrical and electronic applications.

Flame retardancy of electrical and electronic circuitboards (printed wiring boards, PWB) is desirable, and for many such products, firmly required. Underwriters Laboratory (UL) flammability test methods are commonly used, a frequently encountered requirement being passage of the UL 94 test with a V-0 rating which signifies a specified fast extinguishment after ignition by a standard flame. It must be noted that thermomechanical and electrical properties must not be unduly compromised by the flame retardant. Electrical resistance, dielectric properties and the integrity of the copper-to-resin lamination must be retained. Thermal stability during the soldering operations must be adequate.

Many of the printed wiring boards used at present are based on epoxy resins, often glass-reinforced, with laminated copper conductors. It is common practice to include a bromine-based flame retardant, most typically tetrabromobisphenol A, which is reacted into the epoxy resin. Due to environmental concerns over the disposal of scrap electrical and electronic products as well as other similar concerns, there is a strong industrial interest in avoiding the use of bromine-based flame retardants and finding alternatives thereto such as phosphorus-based flame retardant materials.

The use of aromatic alkyl phosphonates as flame retardants in epoxy resins is known. However, the complexity of the multistep processes used for making these phosphonates have been a drawback. Also, the presence of catalyst residues in the product phosphonates has tended to compromise the electrical properties of the flame retarded PWB. It is known that electrical resistivity and resistance to dielectric breakdown are reduced by ionic impurities ("Plastics for Electronics," M. Goosey, ed., Kluwer Academic Publishers, Dordrecht, Netherlands, 1999, pp. 304-5). Other disadvantages of having high ionic (as exemplified by sodium) catalyst levels in an epoxy resin formulation are cited in U.S. Pat. No. 6,037,425, namely, excessively fast cure and difficult temperature control.

The preparation of diphenyl methylphosphonate by reacting triphenyl phosphite with methanol in the presence of a catalytic amount of methyl iodide is known from E. M. Honig and E. D. Weil, J. Org. Chem. 42, 379 (1977) and from U.S. Pat. No. 4,377,537. In the process described by Honig and Weil, phenol by-product is formed and must be removed. A more troublesome by-product, the very unstable diphenyl hydrogenphosphonate, is also formed and an extensive multistep washing procedure is required for its removal. The process typically provides a rather poor yield of product and generates an excessive amount of waste.

U.S. Pat. No. 4,377,537, the entire contents of which are incorporated by reference herein, describes the reaction of methane phosphonic acid dimethyl ester (i.e., dimethyl methylphosphonate) with triphenyl phosphite in the presence of a relatively large amount of methyl iodide (a volatile, costly and highly toxic compound) as catalyst to provide methane phosphonic acid diphenyl ester (i.e., diphenyl methylphosphonate).

U.S. Pat. No. 4,374,971, the entire contents of which are incorporated by reference herein, describes the transesterification of diaryl alkylphosphonate with aromatic diol and, optionally, a branching monomer, in the presence of a neutral ester interchange catalyst such as a $C_1$-$C_{18}$ tetraalkyl titanate, dialkyl tin oxide, dialkyl-dialkoxy tin compound, $C_3$-$C_{18}$ tetralkyl zirconate, $C_2$-$C_{18}$ trialkyl vanadylate, antimony salt, bismuth salt, $C_2$-$C_4$ dialkyl stannic acid ester, $C_2$-$C_4$ trialkyl stannic acid ester or mixture of germanium dioxide or titanium dioxide with at least one of the foregoing to provide aromatic, optionally branched-chain, polyphosphonates (arylene alkylphosphonate polymers) having a number average molecular weight ($M_n$) of 11,000 to 200,000.

U.S. Pat. No. 4,690,964, the entire contents of which are incorporated by reference herein, describes the transesterification of diaryl alkylphosphonate with aromatic diol and, optionally, a branching monomer, in the presence of an alkaline catalyst such as an alkali metal and/or alkaline earth metal alcoholate, phenolate, oxide, amide or salt to provide branched or nonbranched oligomeric polyalkylphosphonates (arylene alkylphosphonate oligomers) having a weight average molecular weight ($M_w$) of about 2,000 to about 10,000.

International Publication No. WO 03/029258, the entire contents of which are incorporated by reference herein, describes the transesterification of diphenyl alkylphosphonate with aromatic diol in the presence of a catalyst such as sodium methylate to provide hydroxy-terminated oligomeric phosphonates useful as reactive fire retardants for epoxy resins.

The oligomer/polymer products provided by the processes of U.S. Pat. Nos. 4,374,971, 4,690,964 and WO 03/029258 may contain amounts of metal catalyst residues which, if not removed (a difficult procedure which adds to cost and because of the high viscosity of the oligomer/polymer, requires special equipment), can be deleterious to the demanding residual electrical properties required for printed wiring board applications.

It is an object of the present invention to provide a high-yield process for the manufacture of diaryl alkylphosphonate.

It is a further object of the invention to provide such a process with little or no requirement for purification steps, and in particular, little if any need for washing and distilling.

It is yet another object of the invention to provide a process for making diaryl alkylphosphonate directly usable for further reaction with aromatic diol to provide an oligomeric and/or polymeric flame retardant exhibiting outstanding properties for use in electronic and electrical printed wiring boards.

SUMMARY OF THE INVENTION

In keeping with the foregoing and other objects of the invention, there is provided a process for preparing a diaryl alkylphosphonate which comprises reacting triaryl phosphite with dialkyl alkylphosphonate in the presence of a catalytically effective amount of a catalyst of the formula $MX_n$ in which M is an alkali metal or alkaline earth metal, X is iodine or bromine and n is equal to the valence of M to provide the diaryl alkylphosphonate.

Further in accordance with this invention, the diaryl alkylphosphonate product obtained by the aforesaid process without separation from the reaction medium in which it is prepared, and preferably without the addition of other or further catalyst, is reacted with a diphenol, and optionally with one or more branching monomers as disclosed in U.S. Pat. No. 4,374,971, to provide an arylene alkylphosphonate oligomer and/or polymer which is particularly suitable as a reactive flame retardant, e.g., for an epoxy resin.

DETAILED DESCRIPTION OF THE INVENTION

The present invention comprises reacting one or more triaryl phosphites with one or more dialkyl alkylphosphonates in the presence of alkali metal iodide to provide diaryl alkylphosphonate.

The aryl groups of the triaryl phosphite reactant can be the same or different and can be phenyl, cresyl, xylenyl, lower-alkylphenyl, naphthyl, halophenyl, and the like. Examples of useful triaryl phosphites include triphenyl phosphite, tris-p-cresyl phosphite, tris-m-cresyl phosphite, tris-p-chlorophenyl phosphite, tri-p-bromophenyl phosphite, tris-p-ethylphenyl phosphite, tris-p-isopropylphenyl phosphite, tris-m-isopropylphenyl phosphite, tris-o-isopropylphenyl phosphite, tris-p-tert-butylphenyl phosphite, tris-p-methoxyphenyl phosphite, tris-(o,m,p)-cresyl phosphite, diphenyl cresyl phosphite, tri-(o,m,p)-isopropylphenyl phosphite, tris-octyl phenyl phosphite, tris-nonyl phenyl phosphite, diphenyl-β-naphthyl phosphite, and the like. Mixtures of these and similar triaryl phosphites can be used. Triphenyl phosphite and the tricresyl phosphites are generally preferred.

The dialkyl alkylphosphonate reactant can have the same or different alkyl group of from 1 to about 12 carbon atoms and can be independently selected from amongst such alkyl groups as methyl, ethyl, propyl, isopropyl, butyl, isobutyl, pentyl, hexyl, octyl, nonyl, decyl, and the like. Examples of useful dialkyl alkylphosphonates include dimethyl methylphosphonate, dimethyl ethylphosphonate, diethyl ethylphosphonate, di-n-propyl methylphosphonate, di-n-propyl n-propylphosphonate, dibutyl butylphosphonate, dipentyl pentylphosphonate, dioctyl octylphosphonate, dimethyl isopropylphosphonate, and the like. For reasons of lower cost and higher reaction rate, dimethyl methylphosphonate is generally preferred.

The triaryl phosphate will ordinarily be reacted with the alkylphosphonate in at least a stoichiometric amount, i.e., in a 2:1 mole ratio. However, if desired, a slight excess of triaryl phosphite can be employed, e.g., up to about 10% molar excess. The presence of small amounts of unreacted triaryl phosphite in the ultimate oligomer/polymer conversion products herein may be beneficial in some applications when, e.g., additional oxidative stability is desirable.

The reaction can be run batchwise or continuously and is preferably carried out in a closed, or sealed, reactor which has been found to provide a diaryl alkylphosphonate reaction product having a greater purity than that attained by conducting the reaction in an open reactor. The pressure in the closed vessel may be atmospheric or somewhat superatmospheric.

The catalyst $MX_n$ for the phosphite-phosphonate reaction is selected from the group consisting of alkali metal iodide, alkali metal bromide, alkaline earth metal iodide, alkali metal bromide, alkaline earth metal iodide, alkaline earth metal bromide and their mixtures. The alkali metal can be any of those in group IA of the Periodic Table and the alkaline earth metal can be any of those in group IIA of the Periodic Table. Preferably, the catalyst is sodium iodide or potassium iodide. The quantity of catalyst can be in the range of from about 0.01 to about 0.5% by weight and preferably from about 0.02 to about 0.2% by weight, of the reaction medium. Smaller amounts of catalyst tend to make the reaction run more slowly while larger amounts of catalyst may have a negative impact on the electrical properties of resins containing the phosphonate reaction product.

The reaction of phosphite and phosphonate can advantageously be carried out in the range of from about 200° C. to about 250° C., and preferably from about 220° C. to about 230° C., for a period of from about 5 to about 50 hours. At lower temperatures, the reaction may be inconveniently slow although increasing the catalyst level can compensate for this to some extent. At higher temperatures, some decomposition of the desired product to undesirable by-products may result.

An important feature of the invention is that the diaryl alkylphosphonate (preferably diphenyl methylphosphonate) is suitable, without purification and in the substantial absence of other or further added catalyst, for further reaction (either immediately or after storage) by reaction with an aromatic diol and, optionally, at least one branching monomer, to form arylene alkylphosphonate oligomer and/or polymer, in particular, an arylene methylphosphonate oligomer and/or polymer preferably possessing at least one terminal phenolic hydroxyl group and therefore suitable as a reactive flame retardant, in particular for an epoxy resin, where it chemically enters into the structure of the resin.

The aromatic diol reactant can be resorcinol, hydroquinone, bisphenol A, bisphenol F, bisphenol S, 4,4-dihydroxybiphenyl, naphthalenediol, a novolac of average diol functionality, and the like. A preferred diol is resorcinol.

The optional branching monomer can be any of those disclosed in U.S. Pat. Nos. 4,374,971 and 4,690,964, e.g., a triaryl phosphate such as triphenyl phosphate, an aromatic trihydroxy or tetrahydroxy compound, and the like, at a level of from about 0.01 to about 3 mole % based on the total amount of diaryl alkylphosphonate.

The oligomeric/polymeric products possess a number average molecular weight ($M_n$) of from about 500 to about 100,000, preferably from about 800 to about 5,000 and more preferably, from about 1,000 to about 2,500, and depending on reactant ratio, can have aromatic phenol end groups or aryloxyphosphonate end groups.

A preferred species, an oligomer/polymer obtained from the reaction of resorcinol with diphenyl methylphosphonate at slightly over 1:1 mole ratio and having at least one phenolic hydroxy end group, is highly suitable for use as a reactive flame retardant for epoxy glass-reinforced printed wiring boards (circuitboards) used in electrical and electronic equipment. The oligomer/polymer is reacted with the epoxy resin to provide a prepolymer which can later be cured in the presence of a curing catalyst at elevated temperature. The general details of this procedure are well known in the art and are described in numerous sources, e.g, U.S. Pat. No. 6,524,709, the entire contents of which are incorporated by reference herein.

An important feature of the present process is that the oligomeric/polymeric products herein, unlike prior art polymeric phosphonates, contain no amount of catalyst which might interfere with their storage per se or in an epoxy blend, or interfere with their subsequent curing when desired by uncatalyzed thermal means or by any of the epoxy curing agents known in the art. The oligomeric/polymeric products, when blended with a typical epoxy resin, e.g., a glycidyl ether of bisphenol A, are typically stable at room temperature for a period of 1-3 months. Heating of the blend to 180-200° C. provides a cure over about 60-90 minutes without the need for a catalyst. With a typical catalytic quantity of 2-methylimidazole, cure can be effected in one hour at 170-180° C.

Typical curing agents such as dicyandiamide and polyethylenepolyamine can also be used.

The following examples are illustrative of the invention.

EXAMPLE 1

This example illustrates the process of the invention for making diaryl alkyphosphonate in an open reactor.

A 20 liter stainless steel reactor with stirrer was charged with 7035 g of triphenyl phosphite (TPP). Air was expelled from the reactor by nitrogen which was then left at a very slight purge to prevent incursion of air. The reactor was then heated via an oil-filled heating jacket. When the temperature reached 74° C., 6.1 g of sodium iodide dissolved in 200 ml of dimethyl methylphosphonate (DMMP) reactant was added. When the temperature in the reactor reached 224° C., slow addition of DMMP was started. After about 15% of the remaining DMMP was added, a slight exotherm was observed. The remaining DMMP was added over 3 hours with little or no exotherm (1409 grams of DMMP were added). At this point, a sample of the reaction mixture was taken and by nmr analysis was found to contain about 88% by weight of diphenyl methylphosphonate (DPMP).

EXAMPLE 2

This example illustrates the process of the invention for making diaryl alkylphosphonate in a sealed reactor.

A 170 liter stainless steel reactor with stirrer was charged with 90.60 kg TPP (291.98 moles). Air was expelled from the reactor by flushing with nitrogen three times. The reactor was then closed and remained so during the synthesis. The reactor was heated to 227° C. with stirring. When the reactor had reached this temperature, a solution of 106.46 g. sodium iodide in 1816.7 DMMP was pumped into the reactor over 30 min. The amount of DMMP used in this step was about 10% of the total amount. A reaction exotherm was noted and was controlled by adjustment of the oil temperature and the rate of addition. After the catalyst solution had been added, 16.214 kg of DMMP was pumped into the reactor and the reaction temperature was controlled at 225±2° C. by adjusting the pumping speed and the heating oil temperature. Addition of the DMMP was completed over 90 minutes. After all of the DMMP had been added, the oil temperature was slowly raised and adjusted to maintain the reaction temperature at about 225° C. Then, 75 minutes after the dosing was completed, a sample was taken from the reactor and analyzed by GC which gave the following results: DPMP 94.6%, TPP 1.9%. To correct for the slight excess of TPP remaining, an additional 290 g DMMP (2.34 moles) was added and the reaction allowed to proceed one hour longer, total running time 11 hours. One hour after this addition, another sample was taken and analyzed by GC: DPMP 96.4%, TPP 0.20%. The yield was 108.8 kg product (substantially the theoretical amount) with the final analysis (after heating was discontinued) DPMP 97.3%, unreacted TPP 0.00%.

EXAMPLE 3

This example illustrates the conversion of the DPMP product of Example 2 in situ to provide oligomeric/polymeric resorcinol methylphosphonate.

A stirred 170 liter stainless steel reactor was used, fitted with a nitrogen sparging inlet, and a packed distillation column feeding into a condenser with facility for tempered water, thence to a receiver, and thence to a vacuum source.

Initially, 38.906 kg of resorcinol was transferred into the reactor. The reactor was closed and for 45 min, vacuum was applied (1 mbar). Then, 88.896 kg (358.1 moles) of DPMP (the crude product prepared in Example 2) was drawn into the reactor by means of the vacuum. The reactor was then opened to introduce an additional 2.508 kg resorcinol, making up a total of 41.414 kg (376.1 moles) resorcinol (mole ratio resorcinol/DPMP=1.05). No catalyst was added.

Heating and stirring was started and air was removed from the free volume of the system by repeated application of vacuum and filling with nitrogen. A small nitrogen purge was also used. The reaction mixture was heated by the reactor's oil heater to the set point temperature of 60° C. and the stirrer was set at 150 rpm. The reactor was kept under nitrogen purge (10 1/min) and heated with stirring to about 231° C. at which point distillation of evolved phenol began. Phenol was distilled off over about 11 hours up to a 241° C. reactor temperature and finally a vacuum of about 0.5 down to 0.02 atmospheres at reactor temperature up to 243° C. was used to complete the removal of phenol.

The product remaining in the reaction vessel was drained while molten. It was determined to be an oligomeric resorcinol methylphosphonate (alternative names: oligomeric m-phenylene methylphosphonate or oligomeric 1,3-phenylene methylphosphonate) of number average molecular weight of about 1200 (and weight average molecular weight of about 1,800). Spectroscopic analysis indicated the presence of phenolic hydroxyl end groups. The yield of oligomer was almost quantitative (65.08 kg). The product was a brittle glass-like solid at room temperature with a softening point of about 40° C.

EXAMPLE 4

This example illustrates the use of the oligomeric resorcinol methylphosphonate of Example 3 as a reactive fire retardant in an epoxy resin intended for electrical/electronic applications.

79.8 wt. % of novolac epoxy resin (epoxy equivalent 176-181) was combined with 20 wt. % of the reaction medium of Example 3 containing molten oligomeric resorcinol methylphosphonate and 20 wt. % of solvent, methylethyl ketone, was added thereto. The mixture was maintained at 60° C. under continuous stirring until a clear uniform solution was obtained. 0.2 wt. % 2-methyl imidazole was then added and heating was discontinued. The material while warm was applied as a varnish to a glass mat to provide a prepreg. After removal of solvent from the prepreg, it and a copper foil were assembled into a laminate which was cured in a press at 130° C. for 30 min. after which further pressure was applied and the laminate further heated at 171° C. for 60 min. The resulting cured laminate possessed a V-0 rating UL-94 and $T_g$ of 150° C. The laminate showed good resistance to delamination of the copper foil in a standard industrial Pressure Cooker Test.

What is claimed:

1. A process for preparing arylene alkylphosphonate oligomer and/or polymer which comprises:
    a) reacting triaryl phosphite with dialkyl alkylphosphonate in the presence of a catalytically effective amount of catalyst of the formula MXn in which M is an alkali metal or alkaline earth metal, X is iodine or bromine and n is equal to the valence of M, optionally, in a closed reactor, to provide diaryl alkylphosphonate; and,
    b) reacting the diaryl alkylphosphonate with aromatic diol and, optionally, at least one branching monomer, in the absence of other or further added catalyst to provide the arylene alkylphosphonate oligomer and/or polymer.

2. The process of claim 1 wherein the diaryl alkylphosphonate of step (a) is reacted without removal of catalyst therefrom with the aromatic diol.

3. The process of claim 1 wherein in step (a) the triaryl phosphite is triphenyl phosphite, the dialkyl alkylphosphonate is dimethyl methylphosphonate, in catalyst MXn, M is sodium, X is iodine and n is equal to 1, the catalyst is present at from about 0.01 to about 0.5% by weight diaryl alkylphosphonate is diphenyl methylphosphonate, and in step (b) the aromatic diol is resorcinol and the arylene alkylphosphonate oligomer and/or polymer is resorcinol methylphosphonate oligomer and/or polymer.

4. The process of claim 3 wherein the diaryl alkylphosphonate of step (a) is reacted without removal of catalyst therefrom with the aromatic diol.

5. The process of claim 1 in which the mole ratio of aromatic diol to diaryl alkyl phosphonate is greater than 1 and the arylene alkylphosphonate oligomer and/or polymer possesses at least one terminal hydroxyl group.

6. The process of claim 2 in which the mole ratio of aromatic diol to diaryl alkyl phosphonate is greater than 1 and the arylene alkylphosphonate oligomer and/or polymer possesses at least one terminal hydroxyl group.

7. The process of claim 3 in which the mole ratio of aromatic diol to diaryl alkyl phosphonate is greater than 1 and the arylene alkylphosphonate oligomer and/or polymer possesses at least one terminal hydroxyl group.

8. The process of claim 4 in which the mole ratio of aromatic diol to diaryl alkyl phosphonate is greater than 1 and the arylene alkylphosphonate oligomer and/or polymer possesses at least one terminal hydroxyl group.

9. The process of claim 1 wherein the arylene alkylphosphonate oligomer and/or polymer has a number average molecular weight of from about 800 to about 5,000.

10. The process of claim 1 wherein the arylene alkylphosphonate oligomer and/or polymer has a number average molecular weight of from about 1,000 to about 2,500.

11. The process of claim 3 wherein the arylene alkylphosphonate oligomer and/or polymer has a number average molecular weight of from about 800 to about 5,000.

12. The process of claim 3 wherein the arylene alkylphosphonate oligomer and/or polymer has a number average molecular weight of from about 1,000 to about 2,500.

13. The process of claim 5 wherein the arylene alkylphosphonate oligomer and/or polymer has a number average molecular weight of from about 800 to about 5,000.

14. The process of claim 5 wherein the arylene alkylphosphonate oligomer and/or polymer has a number average molecular weight of from about 1,000 to about 2,500.

15. The process of claim 7 wherein the arylene alkylphosphonate oligomer and/or polymer has a number average molecular weight of from about 800 to about 5,000.

16. The process of claim 7 wherein the arylene alkylphosphonate oligomer and/or polymer has a number average molecular weight of from about 1,000 to about 2,500.

* * * * *